US011278457B2

(12) United States Patent
Benz et al.

(10) Patent No.: US 11,278,457 B2
(45) Date of Patent: Mar. 22, 2022

(54) INCONTINENCE DETECTION OPTIMIZATION USING DIRECTIONAL WICKING

(71) Applicant: Hill-Rom Services, Inc., Batesville, IN (US)

(72) Inventors: Eric D. Benz, Sunman, IN (US); Charles A. Lachenbruch, Batesville, IN (US); Gavin M. Monson, Oxford, OH (US); Ryan S. Severns, Grand Rapids, MI (US); Dan R. Tallent, Hope, IN (US); Bryan Weidman, Columbus, IN (US); Joshua A. Williams, West Harrison, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 473 days.

(21) Appl. No.: 15/879,865

(22) Filed: Jan. 25, 2018

(65) Prior Publication Data
US 2018/0221216 A1   Aug. 9, 2018

Related U.S. Application Data

(60) Provisional application No. 62/456,903, filed on Feb. 9, 2017.

(51) Int. Cl.
*A61F 13/42* (2006.01)
*A61F 13/537* (2006.01)
(Continued)

(52) U.S. Cl.
CPC ........ *A61F 13/42* (2013.01); *A61F 13/53717* (2013.01); *A61F 2013/15121* (2013.01);
(Continued)

(58) Field of Classification Search
CPC .............................. A61F 13/42; A61B 5/6808
See application file for complete search history.

(56) References Cited

U.S. PATENT DOCUMENTS 3,017,304 A * 1/1962 Burgeni ................ A61F 13/534
428/167
3,767,859 A * 10/1973 Doering ............... A61B 5/0002
379/106.02
(Continued)

FOREIGN PATENT DOCUMENTS

| WO | 99/56687 A1 | 11/1999 | |
| WO | 2006/105305 A1 | 10/2006 | |
| WO | WO-2006105305 A1 * | 10/2006 | ........... A61F 13/533 |

OTHER PUBLICATIONS

Silverio-Fernández et al. Visualization in Engineering (2019) 6:3 https://doi.org/10.1186/s40327-018-0063-8 (Year: 2018).*
(Continued)

*Primary Examiner* — Catharine L Anderson
*Assistant Examiner* — Arjuna P Chatrathi
(74) *Attorney, Agent, or Firm* — Barnes & Thornburg LLP

(57) ABSTRACT

An incontinence detection pad for detecting incontinence events includes a moisture absorbent layer that has non-embossed areas and embossed areas. The non-embossed areas have a first density of fibers of the layer, and the embossed areas have a second density of fibers of the layer that is greater than the first density. The incontinence detection pad further includes a plurality of electrodes positioned beneath the moisture absorbent layer and a transmitter connected to the plurality of electrodes and configured to transmit a signal indicative of a status of the moisture absorbent layer.

20 Claims, 11 Drawing Sheets

(51) Int. Cl.
*A61F 13/15* (2006.01)
*A61F 13/84* (2006.01)
*A61F 13/511* (2006.01)

(52) U.S. Cl.
CPC ............... *A61F 2013/15154* (2013.01); *A61F 2013/424* (2013.01); *A61F 2013/51165* (2013.01); *A61F 2013/8479* (2013.01)

(56) References Cited

U.S. PATENT DOCUMENTS

| | | | |
|---|---|---|---|
| 4,114,621 A | 9/1978 | Mims | |
| 4,559,051 A | 12/1985 | Hanson | |
| 4,592,751 A | 6/1986 | Gegelys | |
| 4,643,726 A | 2/1987 | Gegelys | |
| 4,944,734 A | 7/1990 | Wallach | |
| 4,950,264 A * | 8/1990 | Osborn, III | A61F 13/15203 604/385.08 |
| 4,961,982 A | 10/1990 | Taylor | |
| 5,074,854 A | 12/1991 | Davis | |
| 5,147,345 A | 9/1992 | Young et al. | |
| 5,290,269 A | 3/1994 | Heiman | |
| 5,318,554 A | 6/1994 | Young et al. | |
| 5,350,370 A | 9/1994 | Jackson et al. | |
| 5,366,451 A | 11/1994 | Levesque | |
| 5,387,207 A | 2/1995 | Dyer et al. | |
| 5,562,648 A | 10/1996 | Peterson | |
| 5,562,649 A | 10/1996 | Chauvette et al. | |
| 5,607,414 A | 3/1997 | Richards et al. | |
| 5,632,737 A | 5/1997 | Stone et al. | |
| 5,634,915 A | 6/1997 | Oesterdahl | |
| 5,677,058 A | 10/1997 | Neal et al. | |
| 5,728,085 A | 3/1998 | Widlund et al. | |
| 5,730,737 A | 3/1998 | Widlund et al. | |
| 5,735,145 A | 4/1998 | Pernick | |
| 5,814,034 A | 9/1998 | Widlund et al. | |
| 5,855,571 A | 1/1999 | Steger et al. | |
| 5,903,222 A * | 5/1999 | Kawarizadeh | G01N 27/223 340/604 |
| 5,916,670 A | 6/1999 | Tan et al. | |
| 6,025,782 A * | 2/2000 | Newham | A61B 5/1115 340/573.1 |
| 6,037,518 A | 3/2000 | Guidotti et al. | |
| 6,083,211 A | 7/2000 | DesMarais | |
| 6,097,347 A * | 8/2000 | Duan | H01Q 1/2225 343/802 |
| 6,284,942 B1 | 9/2001 | Rabin | |
| 6,465,712 B1 | 10/2002 | Matthews et al. | |
| 6,495,734 B1 | 12/2002 | Fields et al. | |
| 6,534,149 B1 | 3/2003 | Daley et al. | |
| 6,545,195 B2 | 4/2003 | Chmielewski | |
| 6,569,133 B2 | 5/2003 | Cheng et al. | |
| 6,649,809 B2 | 11/2003 | Fields et al. | |
| 6,685,684 B1 | 2/2004 | Falconer | |
| 6,706,944 B2 | 3/2004 | Qin et al. | |
| 6,727,196 B2 | 4/2004 | Yahiaoui et al. | |
| 6,835,192 B1 | 12/2004 | Guidotti et al. | |
| 6,863,933 B2 | 3/2005 | Cramer et al. | |
| 6,900,249 B2 | 5/2005 | Mork et al. | |
| 6,905,986 B2 | 6/2005 | Ranganathan et al. | |
| 6,984,439 B2 | 1/2006 | Topolkaraev | |
| 7,048,725 B2 | 5/2006 | Kling et al. | |
| 7,686,921 B2 | 3/2010 | Hamed et al. | |
| 7,812,062 B2 | 10/2010 | Strandburg et al. | |
| 8,591,488 B2 | 11/2013 | Brezoczky et al. | |
| 8,629,315 B2 | 1/2014 | Miura et al. | |
| 8,784,857 B2 | 7/2014 | Savage | |
| 8,914,923 B2 * | 12/2014 | Smith | A47C 27/008 5/484 |
| 9,028,460 B2 | 5/2015 | Medeiros | |
| 9,278,034 B2 | 3/2016 | Brezoczky et al. | |
| 9,322,797 B1 | 4/2016 | Lastinger et al. | |
| 9,366,644 B1 | 6/2016 | Lastinger et al. | |
| 9,445,740 B1 * | 9/2016 | Crone | A61B 5/282 |
| 9,506,886 B1 | 11/2016 | Woodbury et al. | |
| 9,511,167 B2 | 12/2016 | Nonni et al. | |
| 9,719,951 B1 | 8/2017 | Woodbury et al. | |
| 9,810,652 B1 | 11/2017 | Lastinger et al. | |
| 9,910,003 B1 | 3/2018 | Lastinger et al. | |
| 10,134,489 B2 * | 11/2018 | Lai | G06K 19/0716 |
| 2004/0043369 A1 * | 3/2004 | Pawar | A61F 13/42 434/267 |
| 2005/0099294 A1 * | 5/2005 | Bogner | G16H 40/63 340/540 |
| 2008/0132859 A1 * | 6/2008 | Pires | A61F 13/42 604/361 |
| 2013/0019405 A1 * | 1/2013 | Flanagan | G16H 40/63 5/600 |
| 2015/0119656 A1 * | 4/2015 | Foster | A61B 5/746 600/301 |
| 2016/0267769 A1 * | 9/2016 | Rokhsaz | H01Q 9/04 |
| 2016/0374626 A1 | 12/2016 | Heil et al. | |
| 2017/0065464 A1 | 3/2017 | Heil et al. | |
| 2017/0098044 A1 | 4/2017 | Lai et al. | |
| 2017/0246063 A1 | 8/2017 | Monson et al. | |
| 2018/0021184 A1 | 1/2018 | Monson et al. | |

OTHER PUBLICATIONS

Extended EP Search Report for European Patent Application No. EP18154717.5 dated Apr. 4, 2018; 7 pages.

\* cited by examiner

| BED ID | LOCATION | SECONDARY DEVICE |
|---|---|---|
| S/N 01234567 | ROOM 501 | MAC 00:15:24:A4:43:01 |
| MAC 00:17:23:E0:09:A4 | ROOM 502 | MAC 00:15:24:A4:43:02 |
| S/N 12345678 | ROOM 503 | MAC 00:15:24:A4:43:23 |
| S/N 23456789 | ROOM 504 | MAC 00:15:24:A4:43:03 |

INCONTINENCE DETECTION OPTIMIZATION USING DIRECTIONAL WICKING

The present application claims the benefit, under 35 U.S.C. § 119(e), of U.S. Provisional Application No. 62/456,903, which was filed Feb. 9, 2017, and which is hereby incorporated by reference herein in its entirety.

BACKGROUND

The present disclosure relates to incontinence pads that sense patient incontinence. More specifically, the present disclosure relates to disposable incontinence pads of hospital beds, medical beds, or other types of beds in which the disposable incontinence pads are designed to absorb liquid in case of incontinent events.

In a care facility, such as a hospital or a nursing home, patients are often placed on patient support apparatuses for an extended period of time. Some patients who are positioned on the patient support apparatuses may have a risk of developing certain skin conditions, such as bed sores (also known as pressure sores or decubitus ulcers), due to heat and moisture present at the interface of the patient and the surface of a bed mattress. In an effort to mitigate or prevent such conditions, some bed mattresses have a built-in microclimate structure. While various microclimate management systems have been developed, in certain applications there is still room for improvement. Thus, a need persists for further contributions in this area of technology.

SUMMARY

The present application discloses one or more of the features recited in the appended claims and/or the following features which, alone or in any combination, may comprise patentable subject matter:

According to a first aspect of the present disclosure, an incontinence detection pad comprises a moisture absorbent layer, a plurality of electrodes positioned beneath the moisture absorbent layer, and a transmitter connected to the plurality of electrodes and configured to transmit a signal indicative of a status of the moisture absorbent layer. The moisture absorbent layer includes (i) non-embossed areas with a first density of fibers of the moisture absorbent layer and (ii) embossed areas with a second density of fibers of the moisture absorbent layer. The second density is greater than the first density.

In some embodiments, the embossed areas are configured to draw moisture toward a peripheral region of the incontinence detection pad.

In some embodiments, the incontinence detection pad further includes a top layer positioned atop the moisture absorbent layer. The top layer includes a nonwoven moisture-wicking material that is oriented horizontally along the top layer.

In some embodiments, the plurality of electrodes is printed on a barrier layer positioned underneath the moisture absorbent layer.

In some embodiments, the moisture absorbent layer includes a moisture absorbent material forming an increasing density gradient. The increasing density gradient is formed from a top surface to a bottom surface of the moisture absorbent layer.

In some embodiments, the transmitter is a Radio Frequency Identification (RFID) tag.

In some embodiments, the transmitter is configured to communicate with a reader that evaluates the transmitted signal to determine the status of the moisture absorbent layer.

In some embodiments, the reader is an RFID reader.

In some embodiments, the reader is further configured to wirelessly communicate with a server to alert a caregiver of the status of the moisture absorbent layer.

In some embodiments, the server is included in a nurse call system.

In some embodiments, the server is included in an electronic medical record (EMR) system.

In some embodiments, the server is configured to communicate with a mobile device of a caregiver.

In some embodiments, the server is configured to communicate with a smart device of a caregiver.

In some embodiments, the reader is further configured to communicate with a server to alert a caregiver of the status of the moisture absorbent layer via a wired connection.

In some embodiments, the wired connection comprises a nurse call cable.

In some embodiments, the reader is further configured to communicate with a notification system to alert a caregiver of the status of the moisture absorbent layer.

In some embodiments, the embossed areas are compressed into a pre-determined pattern.

In some embodiments, the embossed areas form a sinusoidal wave pattern.

In some embodiments, the embossed areas form a zig-zag pattern.

In some embodiments, the embossed areas form a pattern having non-intersecting lines.

In some embodiments, the embossed areas form a pattern having non-intersecting lines that horizontally extend along the moisture absorbent layer.

According to a second aspect of the present disclosure, an incontinence detection pad comprises a moisture absorbent layer, a top layer positioned atop the moisture absorbent layer having a moisture absorbent material, embossed areas formed by compressing the top layer and the moisture absorbent layer, a plurality of electrodes positioned beneath the moisture absorbent layer, and a transmitter connected to the plurality of electrodes and configured to transmit a signal indicative of a status of the moisture absorbent layer. The top layer includes a nonwoven moisture-wicking material that is oriented horizontally along the top layer. The top layer and the moisture absorbent layer include (i) non-embossed areas have a first density of fibers of the moisture absorbent layer and (ii) the embossed areas have a second density of fibers of the moisture absorbent layer that is greater than the first density.

In some embodiments, the embossed areas are configured to draw moisture toward a peripheral region of the incontinence detection pad.

In some embodiments, the embossed areas are compressed into a pre-determined pattern.

In some embodiments, the embossed areas form a sinusoidal wave pattern.

In some embodiments, the embossed areas form a zig-zag pattern.

In some embodiments, the embossed areas form a pattern having non-intersecting lines.

In some embodiments, the embossed areas form a pattern having non-intersecting lines that horizontally extend along the moisture absorbent layer.

In some embodiments, the plurality of electrodes is printed on a barrier layer positioned underneath the moisture absorbent layer.

In some embodiments, the moisture absorbent material forms an increasing density gradient. The increasing density gradient is formed from a top surface to a bottom surface of the moisture absorbent layer.

In some embodiments, the transmitter is a Radio Frequency Identification (RFID) tag.

In some embodiments, the transmitter is configured to communicate with a reader that evaluates the transmitted signal to determine the status of the moisture absorbent layer.

In some embodiments, the reader is an RFID reader.

In some embodiments, the reader is further configured to wirelessly communicate with a server to alert a caregiver of the status of the moisture absorbent layer.

In some embodiments, the server is included in a nurse call system.

In some embodiments, the server is included in an electronic medical record (EMR) system.

In some embodiments, the server is configured to communicate with a mobile device of a caregiver.

In some embodiments, the server is configured to communicate with a smart device of a caregiver.

In some embodiments, the reader is further configured to communicate with a server to alert a caregiver of the status of the moisture absorbent layer via a wired connection.

In some embodiments, the wired connection comprises a nurse call cable.

In some embodiments, the reader is further configured to communicate with a notification system to alert a caregiver of the status of the moisture absorbent layer.

According to a third aspect of the present disclosure, an incontinence detection pad comprises a moisture absorbent layer, a plurality of moisture absorbent blocks, a plurality of electrodes positioned beneath the moisture absorbent layer, and a transmitter connected to the plurality of electrodes and configured to transmit a signal indicative of a status of the moisture absorbent layer. The moisture absorbent layer includes (i) non-embossed areas with a first density of fibers of the moisture absorbent layer and (ii) embossed areas with a second density of fibers of the moisture absorbent layer. The second density is greater than the first density. The plurality of moisture absorbent blocks is positioned on each side of the moisture absorbent layer. The moisture absorbent blocks includes a moisture absorbent material.

In some embodiments, the moisture absorbent layer extends into the moisture absorbent block such that the moisture absorbent block absorbs the moisture from the moisture absorbent layer.

In some embodiments, the embossed areas are configured to draw moisture toward the plurality of moisture absorbent blocks.

In some embodiments, the incontinence detection pad further includes a top layer positioned atop the moisture absorbent layer. The top layer includes a nonwoven moisture-wicking material that is oriented horizontally along the top layer.

In some embodiments, the plurality of electrodes is printed on a barrier layer positioned underneath the moisture absorbent layer.

In some embodiments, the moisture absorbent layer includes a moisture absorbent material forming an increasing density gradient. The increasing density gradient is formed from a top surface to a bottom surface of the moisture absorbent layer.

In some embodiments, the transmitter is included in a Radio Frequency Identification (RFID) tag.

In some embodiments, the transmitter is configured to communicate with a reader that evaluates the transmitted signal to determine the status of the moisture absorbent layer.

In some embodiments, the reader is an RFID reader.

In some embodiments, the reader is further configured to wirelessly communicate with a server to alert a caregiver of the status of the moisture absorbent layer.

In some embodiments, the server is included in a nurse call system.

In some embodiments, the server is included in an electronic medical record (EMR) system.

In some embodiments, the server is configured to communicate with a mobile device of a caregiver.

In some embodiments, the server is configured to communicate with a smart device of a caregiver.

In some embodiments, the reader is further configured to communicate with a server to alert a caregiver of the status of the moisture absorbent layer via a wired connection.

In some embodiments, the wired connection comprises a nurse call cable.

In some embodiments, the reader is further configured to communicate with a notification system to alert a caregiver of the status of the moisture absorbent layer.

In some embodiments, the embossed areas are compressed into a pre-determined pattern.

In some embodiments, the embossed areas form a sinusoidal wave pattern.

In some embodiments, the embossed areas form a zig-zag pattern.

In some embodiments, the embossed areas form a pattern having non-intersecting lines.

In some embodiments, the embossed areas form a pattern having non-intersecting lines that horizontally extend along the moisture absorbent layer.

According to a fourth aspect of the present disclosure, an incontinence detection pad comprises a moisture absorbent layer, a plurality of electrodes positioned beneath the moisture absorbent layer, a transmitter connected to the plurality of electrodes and configured to transmit a signal indicative of a status of the moisture absorbent layer, and a microclimate layer positioned between the moisture absorbent layer and the plurality of electrodes. The moisture absorbent layer includes (i) non-embossed areas with a first density of fibers of the moisture absorbent layer and (ii) embossed areas with a second density of fibers of the moisture absorbent layer. The second density is greater than the first density. The microclimate layer includes a three-dimensional material that is configured to conduct air between the moisture absorbent layer and the plurality of electrodes.

In some embodiments, the microclimate layer is configured to be coupled to a blower.

In some embodiments, the embossed areas are configured to draw moisture toward a peripheral region of the incontinence detection pad.

In some embodiments, the embossed areas are compressed into a pre-determined pattern.

In some embodiments, the embossed areas form a sinusoidal wave pattern.

In some embodiments, the embossed areas form a zig-zag pattern.

In some embodiments, the embossed areas form a pattern having non-intersecting lines.

In some embodiments, the embossed areas form a pattern having non-intersecting lines that horizontally extend along the moisture absorbent layer.

According to a fifth aspect of the present disclosure, an apparatus for modifying the temperature of a person's skin in a localized region comprises a skin contacting layer, a moisture absorbent layer atop the skin contacting layer, and a moisture absorbent material positioned at a perimeter of the layer. The moisture absorbent layer atop the skin contacting layer includes (i) non-embossed areas with a first density of fibers of the moisture absorbent layer and (ii) embossed areas with a second density of fibers of the moisture absorbent layer. The second density is greater than the first density.

In some embodiments, the skin contacting layer is capable of adhering to the person's skin surrounding an anatomic site.

In some embodiments, the embossed areas extend from a center of the moisture absorbent layer toward the moisture absorbent material at the perimeter of the moisture absorbent layer.

According to a sixth aspect of the present disclosure, an incontinence detection pad comprises a moisture absorbent layer, a plurality of electrodes positioned beneath the moisture absorbent layer, a transmitter connected to the plurality of electrodes and configured to transmit a signal indicative of a status of the moisture absorbent layer, and a resistor inductor unit positioned between the plurality of electrodes and the transmitter.

In some embodiments, the transmitter includes a tamper input.

According to a seventh aspect of the present disclosure, an incontinence detection pad comprises a moisture absorbent layer, a plurality of electrodes positioned beneath the moisture absorbent layer, a transmitter connected to the plurality of electrodes and configured to transmit a signal indicative of a status of the moisture absorbent layer, and a resonant stub positioned between the plurality of electrodes and the transmitter.

In some embodiments, the resonant stub comprises a quarter wave resonant stub.

In some embodiments, the transmitter includes a tamper input.

According to an eighth aspect of the present disclosure, an incontinence detection pad comprises a moisture absorbent layer, a plurality of electrodes positioned beneath the moisture absorbent layer, a transmitter connected to the plurality of electrodes and configured to transmit a signal indicative of a status of the moisture absorbent layer, an antenna, a matching and pairing network, and a resonant stub positioned between the plurality of electrodes and the transmitter.

In some embodiments, the transmitter includes a tamper input.

According to a ninth aspect of the present disclosure, a method of pairing a primary device with a secondary device comprises (i) receiving a request from the secondary device that the secondary device is seeking a corresponding primary device, (ii) monitoring a plurality of primary devices connected to the server for a key, (iii) detecting a primary device with the key, (iv) pairing the secondary device with the primary device such that the secondary device is associated with a location of the primary device, and (v) transmitting a verification of the pairing to the secondary device.

In some embodiments, the key comprises a predefined action of the primary device.

In some embodiments, the key is predefined by a manufacturer, a provider, or a user.

In some embodiments, the key is defined by a sequence of events to transmit data from a primary device that are unlikely to occur on any other primary devices.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
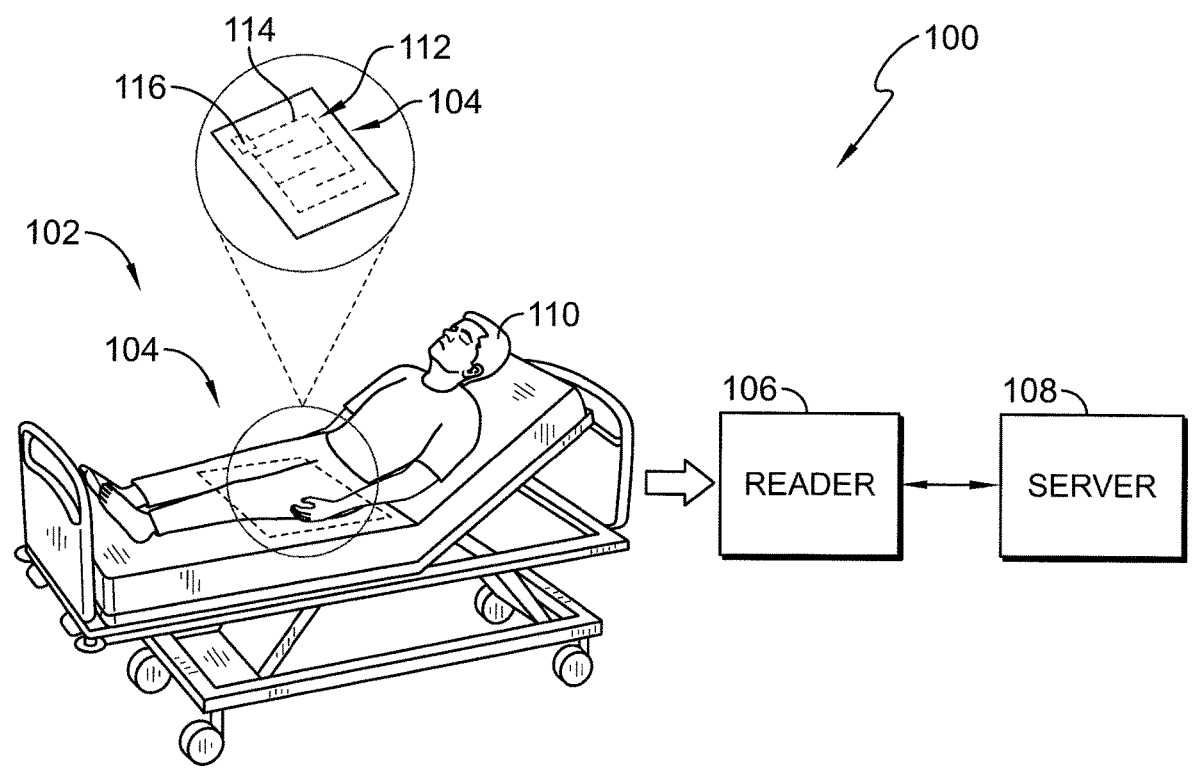
FIG. 1 is a schematic perspective view of a moisture detection system including a patient support apparatus and an incontinence detection pad positioned on the patient support apparatus for detecting moisture presence.

For the purposes of promoting an understanding of the principles of the invention, reference will now be made to one or more illustrative embodiments shown in the drawings and specific language will be used to describe the same. It will nevertheless be understood that no limitation of the scope of the invention is thereby intended. The incontinence detection systems described herein are able to detect biofluids such as blood, urine, fecal matter, interstitial fluid, saline, or any other fluid having a large concentration of ions that easily conduct electricity. The term "incontinence" as used herein is intended to cover all of these biofluids.

Referring now to FIG. 1, an illustrative incontinence detection system 100 to detect moisture presence indicative of an incontinence event is shown. The incontinence detection system 100 includes a patient support apparatus 102, an incontinence detection pad 104, a reader 106, and a server 108. The illustrative patient support apparatus 102 is embodied as a hospital bed. It should be appreciated that in some embodiments, the patient support apparatus 102 may be embodied as a residential bed, a chair, a wheelchair, a mattress, a stretcher, a patient transport device, or any other type of person support apparatus.

The illustrative incontinence detection pad 104 of FIG. 1 is configured to provide a directional wicking of any biofluids of a patient, such as sweat or urine in the case of an incontinent event, to draw the moisture away from the patient 110. To do so, the incontinence detection pad 104 is adapted to support a patient 110 lying on the patient support apparatus 102. Specifically, the incontinence detection pad 104 is positioned atop the patient support apparatus 102 and configured to underlie a body area of the patient 110 supported on the patient support apparatus 102 that is prone to moisture buildup, for example, a patient's pelvic region. Of course, it should be appreciated that the incontinence detection pad 104 may be freely movable on the patient support apparatus 102 to be positioned in an area or zone in which it is desired to conduct surveillance for unwanted moisture or other moisture related abnormalities. In other embodiments, the incontinence detection pad 104 may be integrated into the patient support apparatus 102, such as a mattress. In still other embodiments, the incontinence detection pad 104 may be integrated within an undergarment or other article of clothing or the incontinence detection pad 104 itself is a diaper or disposable undergarment.

The incontinence detection pad 104 further includes a moisture detection sensor system 112 for detecting the presence of moisture. The illustrative moisture detection sensor system 112 includes a plurality of electrodes 114 and a moisture sensor 116. The plurality of electrodes 114 is connected to and extends from the moisture sensor 116, which is discussed in detail below. In the illustrative embodiment, the moisture sensor 116 is embodied as an RFID (Radio Frequency Identification) tag 116. It should be appreciated that in some embodiments, the moisture sensor 116 may be any sensor that is capable of detecting the moisture presence. The RFID tag 116 used in the incontinence pad 104 is a passive tag or chip that communicates with an associated reader 106 by using the electromagnetic field generated by one or more antennae of the reader 106 to power the RFID tag 116. In some embodiments, a semi-passive or active RFID tag 116 is used. The RFID tag 116 is configured to communicate with RFID reader 106 to send stored data, and the reader 106 or other processing circuitry determines whether the incontinence detection pad 104 is wet or dry by evaluating the data transmitted from the RFID tag 116.

In the illustrative example, the reader 106 is configured to communicate a moisture event to the server 108, for example, a server included in a nurse call system and/or an EMR (electronic medical record) system or even a server configured to communicate with a caregiver's mobile or smart device. In some embodiments, the reader 106 may communicate via Wi-Fi antenna or other known wireless communication equipment and protocols. Alternatively or additionally, the reader 106 may communicate the moisture event via a wired connection, such as a nurse call cable. In some embodiments, the incontinence detection system 100 may further include an alert module (not shown) on bed 102 or nearby bed 102 for alerting detected incontinence events.

Figure 2:
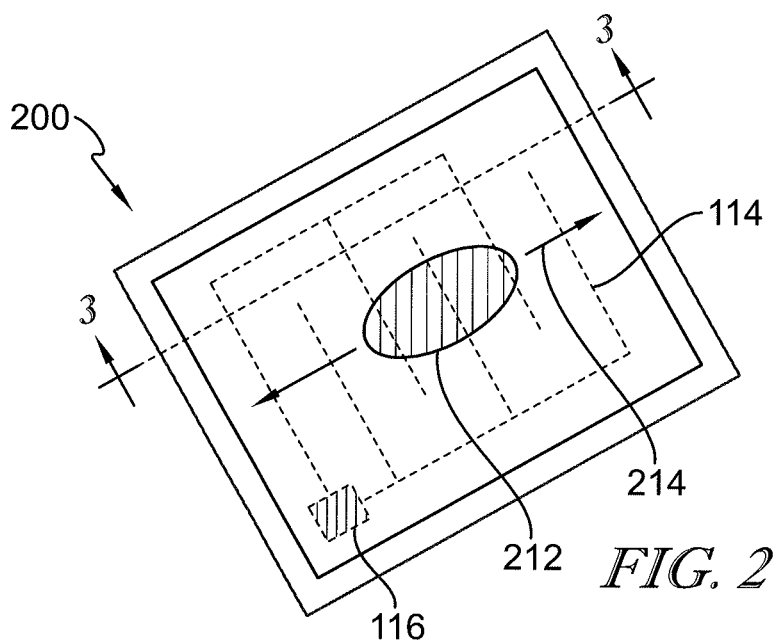
FIG. 2 is a schematic perspective view of a first embodiment of an incontinence detection pad for detecting moisture presence indicative of an incontinence event.
Figure 3:
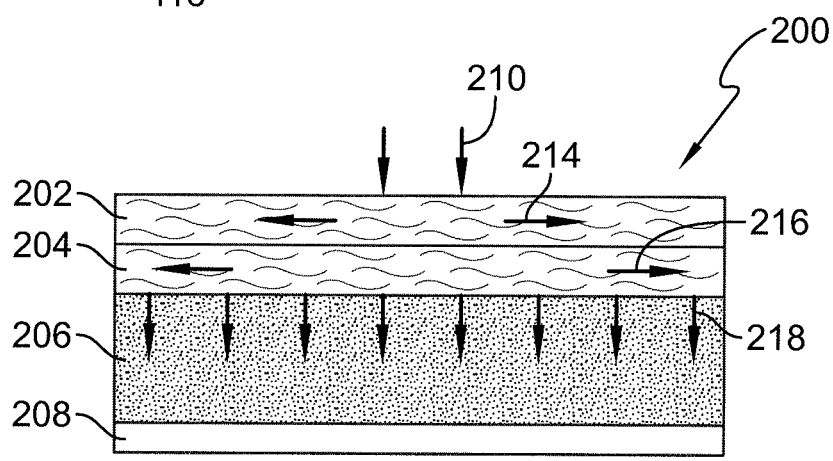
FIG. 3 is a cross-sectional view of the incontinence detection pad of FIG. 2.

Referring now to FIGS. 2 and 3, an illustrative embodiment of an incontinence detection pad 200 includes an acquisition layer 202, a distribution layer 204, an absorbent layer 206, a barrier layer 208, and a moisture detection sensor system 112 implemented as a part of the barrier layer 208. The incontinence detection pad 200 further includes a targeted region 212. In use, the targeted region 212 of the incontinence detection pad 200 is configured to be positioned underneath the patient's pelvic region or other body region that is susceptible to moisture buildup in order to draw the moisture away from the patient.

The acquisition layer 202 includes a moisture-wicking material that is horizontally oriented within the acquisition layer 202. For example, in the illustrative embodiment, the moisture-wicking material is nonwoven and non-linear polymeric or pulp fibers that are horizontally oriented into a nonwoven web structure. The orientation of the moisture-wicking material of the acquisition layer 202 is adapted to provide capillary action or wicking properties to direct moisture in a horizontal direction to draw the moisture toward peripheral regions of the acquisition layer 202. In some embodiments, the moisture-wicking material may form a density gradient across the acquisition layer 202 such that a density of the moisture-wicking material increases from a center to the peripheral regions of the acquisition layer 202. In such embodiment, the density gradient of the moisture-wicking material provides a further capillary action to direct moisture in the horizontal direction to draw the moisture from the center toward the peripheral regions of the acquisition layer 202. The remaining moisture or liquid in the acquisition layer 202 travels downwardly (e.g., by the force of gravity) into the distribution layer 204 to further provide the moisture wicking in the direction towards peripheral region of the incontinence detection pad 200.

Similar to the acquisition layer 202, the distribution layer 204 also includes a moisture-wicking material that is horizontally oriented within the distribution layer 204. For example, in the illustrative embodiment, the moisture-wicking material is nonwoven and non-linear polymeric or pulp fibers that are horizontally oriented into a nonwoven web structure. The orientation of the moisture-wicking material of the distribution layer 204 is adapted to provide capillary action or wicking properties to direct moisture in a horizontal direction to draw the moisture toward peripheral regions of the distribution layer 204. In some embodiments, the moisture-wicking material may form a density gradient across the distribution layer 204 such that a density of the moisture-wicking material increases from a center to the peripheral regions of the distribution layer 204. In such embodiment, the density gradient of the moisture-wicking material provides a further capillary action to direct moisture in the horizontal direction to draw the moisture from the center toward the peripheral regions of the distribution layer 204. It should be appreciated that in some embodiments, the acquisition layer 202 and the distribution layer 204 may be combined into one layer.

The absorbent layer 206 includes an absorbent material, such as a three-dimensional fibrous or woven material. For example, the absorbent layer 206 may be made of a super absorbent polymer (SAP) material which provides 3-5 times more moisture absorption than the materials of the acquisition and/or distribution layers 202, 204 described above. In the illustrative embodiment, the absorbent material is arranged within the absorbent layer 206 to form a density gradient to provide capillary action or wicking properties to direct moisture away from a targeted region 212. For example, an increasing density gradient is preferably formed from the targeted region 212 outwardly toward peripheral regions of the incontinence detection pad 200. In some embodiments, an increasing density gradient is also formed downwardly or vertically from an upper surface to a bottom surface of the absorbent layer 206. Such vertical arrangement of the absorbent material provides capillary action or wicking properties to direct moisture in a vertical direction. The absorbent layer 206 is configured to absorb the moisture and draw the moisture downwardly toward the moisture detection sensor system 112 of the barrier layer 208 as indicated by arrows 218.

The barrier layer 208 is made of an impermeable material which provides a barrier to prevent moisture penetration to a support surface or frame beneath the incontinence detection pad 200. For example, in the illustrative embodiment, the impermeable material is polyethylene (PE). In other embodiments, the impermeable material may be polypropylene (PP) sheets and/or polyurethane (PU) sheets. The barrier layer 208 may or may not be breathable. In some embodiments, the barrier layer 208 may be substantially waterproof. As discussed above, the barrier layer 208 further includes a moisture detection sensor system 112 for detecting moisture presence and, in some embodiments, moisture volume.

In use, the targeted region 212 of the incontinence detection pad 200 is configured to be positioned underneath the patient's body area that is susceptible to moisture buildup. Any patient moisture or liquid travels downwardly (e.g., by the force of gravity) as indicated by arrows 210 into the acquisition layer 202. Once the moisture is in the acquisition layer 202, the nonwoven moisture-wicking material of the acquisition layer 202 is adapted to draw the moisture away from the targeted region 212 in the direction of fiber orientation towards the peripheral regions of the incontinence detection pad 200 as indicated by arrows 214. As discussed above, the acquisition layer 202 is configured to permit a transmission of the moisture to the distribution layer 204 to further provide the moisture wicking in the direction towards the peripheral region of the incontinence detection pad 200 as indicated by arrows 216. The remaining moisture or liquid then travels downwardly (e.g., by the force of gravity) as indicated by arrows 218 into the absorbent layer 206. As discussed above, the absorbent layer 206 is configured to absorb the moisture and draw the moisture downwardly toward a bottom of the absorbent layer 206 towards the moisture detection sensor system 112 of the barrier layer 208.

Figure 4:
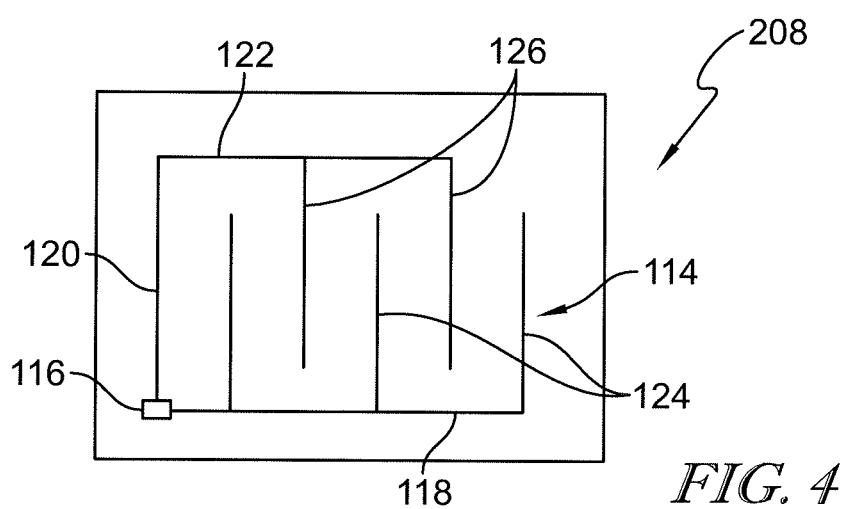
FIG. 4 is a plan view of a barrier layer of the incontinence detection pad of FIGS. 2 and 3 having a moisture detection system.

Referring now to FIG. 4, a detailed diagram of the moisture detection sensor system 112 of the barrier layer 208 is shown. The moisture detection sensor system 112 includes a plurality of electrodes 114 and a moisture sensor 116. The electrodes 114 are made of a conductive material, such as, carbon, silver, copper, zinc and graphene. In the illustrative embodiment, the plurality of electrodes 114 is printed directly onto a top surface of the barrier layer 208 that faces the absorbent layer 206. In some embodiments, the plurality of electrodes 114 may be embedded in the barrier layer 208. In other embodiments, the plurality of electrodes 114 may be embedded in a bottom surface of the absorbent layer 206.

As shown in FIG. 4, a first set of electrode segments 120, 122, 126 is connected to a first end of the moisture sensor 116, and a second set of electrode segments 118, 124 is connected to a second end of the moisture sensor 116. Specifically, the plurality of electrodes 114 includes an electrode segment 118 that extends along a length of the barrier layer 208 and an electrode segment 120 that extends along a width of the barrier layer 208, such that the electrode segment 118 and the electrode segment 120 are perpendicular to one another. The plurality of electrodes 114 further includes an electrode segment 122 that extends perpendicular to the electrode segment 120 along the length of the barrier layer 208 such that the electrode segment 122 is parallel to the electrode segment 118. The electrode segment 118 further includes electrode segments 124 that extend from the electrode segment 118 toward the electrode segment 122. The electrode segment 122 further includes electrode segments 126 that extend from the electrode segment 122 toward the electrode segment 118. The electrode segments 124, 126 are interdigitated to enhance the ability of the moisture sensor 116 to detect areas of moisture that may be oriented between the electrode segments 118, 122.

In use, the moisture sensor 116 applies a voltage to the plurality of electrodes 114. If a sufficient volume of moisture or liquid is collected to span a gap between at least one of the first set of the electrode segments 120, 122, 126 and at least one of the second set of the electrode segments 118, 124, an electrical current passes through the moisture from one electrode segment to another electrode segment, and the moisture sensor 116 detects the moisture presence. Such sufficient volume of moisture falls within a detection range of the moisture detection sensor system 112 and defines a sensitivity of the moisture detection sensor system 112.

It should be appreciated that the moisture volume required depends on how quickly the collected moisture can spread out between the electrode segments 114. For example, in an embodiment of a moisture detection pad that has no moisture wicking properties, moisture spreads out from an origin of the source in all directions generally equally, creating a generally circular wicking shape. In contrast, as discussed above, the combination of the horizontal orientation of the nonwoven material of the acquisition and distribution layers 202, 204 and the horizontal density gradient of the absorbent material of the absorbent layer 206 of the incontinence detection pad 200 enhances the wicking property of the incontinence detection pad 200 and draws moisture in the horizontal direction 214, shown in FIG. 2, from the targeted region 212. As such, the directional wicking property of the moisture detection pad 200 quickly spreads out the collected moisture horizontally in direction 214 between the vertical electrode segments 124, 126 or between any one of the first set of the electrode segments 120, 122, 126 and any one of the second set of electrode segments 118, 124 for faster detection than if no density gradient were provided.

The density gradient also allows the moisture detection sensor system 112 to implement a narrower detection range to avoid false positives (i.e., a determination that an incontinence event such as a bowel movement or urination occurred when it did not) caused by perspiration. For example, if the detection range is too broad, a small amount of sweat or other biofluid that is not related to an incontinence event but which may otherwise complete and connect two electrodes. This is especially true at the lower end of the range. For example, in some embodiments, a moisture volume required for the moisture detection sensor system 112 to detect the presence of moisture is between 20-80 milliliters. In such case, for a patient who normally secretes about 20 milliliters of sweat or other biofluid that is not related to an incontinence event will constantly generate false positives. It should be appreciated that with the enhanced wicking properties, the moisture volume required for the moisture detection sensor system 112 to detect the presence of moisture may be narrowed, for example, 40-80 milliliters, such that 20 milliliters of sweat would not generate a false positive, thereby reducing a number of false positives. By reducing the number of false positives, caregivers such as nurses may reduce the amount of time spent investigating whether detections of incontinence events are erroneous and focus more of their time on removing soiled sheets, garments, and other materials from patients who have actually experienced an incontinence event.

Figure 5:
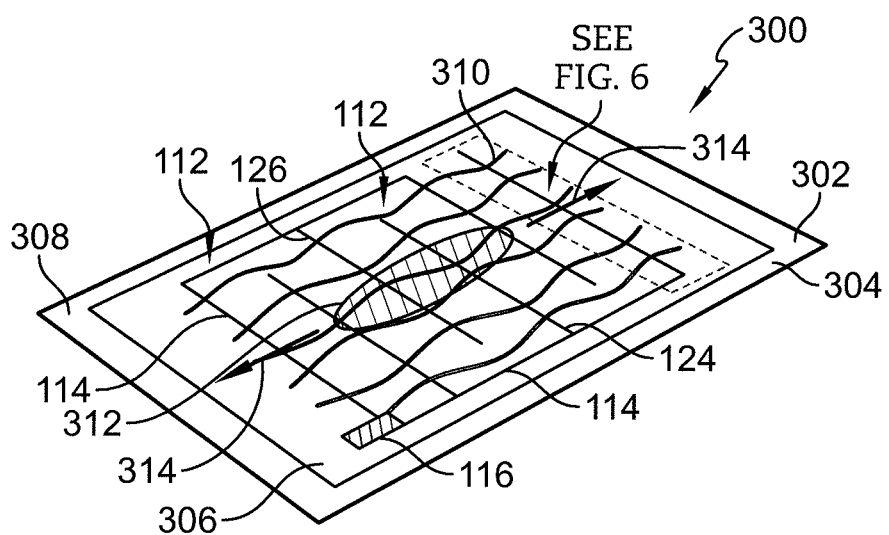
FIG. 5 is a schematic perspective view of a second embodiment of an incontinence detection pad having compressed embossed areas.
Figure 6:
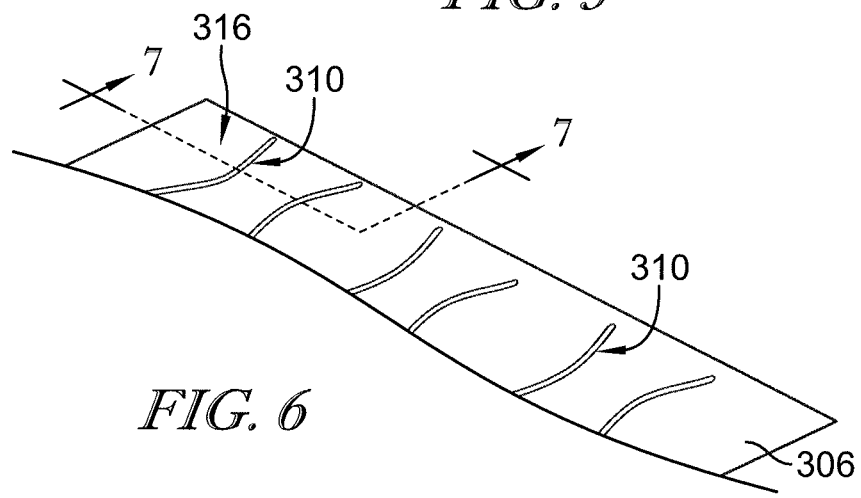
FIG. 6 is a plan view of a portion of the embossed areas of the incontinence detection pad of FIG. 5.
Figure 7:
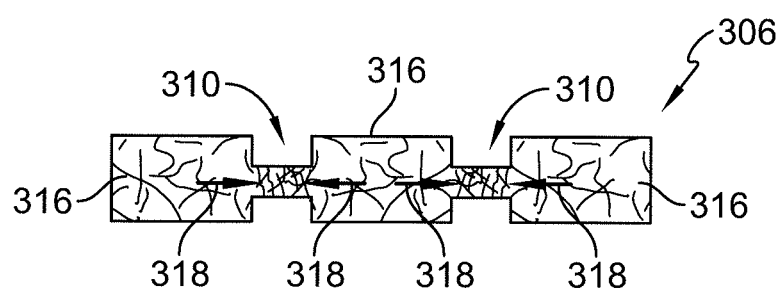
FIG. 7 is a cross-sectional view of a portion the incontinence detection pad of FIGS. 5 and 6 taken along the line 7-7 of FIG. 6.

Referring now to FIGS. 5-7, an alternative embodiment of an incontinence detection pad 300 is shown. The incontinence detection pad 300 includes a targeted region 312, an acquisition layer 302, a distribution layer 304, an absorbent layer 306, a barrier layer 308, and a moisture detection sensor system 112 implemented as a part of the barrier layer 308. In use, similar to the incontinence detection pad 200, the targeted region 312 of the incontinence detection pad 300 is positioned underneath the patient's pelvic region or other body region that is susceptible to moisture buildup to draw the moisture away from the patient toward the moisture detection sensor system 112. It should be appreciated that the moisture sensor system of the incontinence detection pad 300 illustrated in FIGS. 5-7 is substantially similar to the moisture sensor system of the incontinence detection pad 200 discussed above in reference to the embodiment of FIGS. 2-4. Such features are designated in FIGS. 5-7 with the same reference numbers as those used in FIGS. 2-4.

In addition, the acquisition layer 302, the distribution layer 304, and the barrier layer 308 have similar properties and characteristics as the acquisition layer 202, the distribution layers 204, and the barrier layer 208 of FIGS. 2-4, respectively. For example, the acquisition layer 402, similar to the acquisition layer 202 of FIGS. 2-3, includes a nonwoven moisture-wicking material that is configured to provide capillary action or wicking properties to direct moisture in a horizontal direction. The distribution layer 404, similar to the distribution layer 204 of FIGS. 2-3, includes a nonwoven moisture-wicking material that is configured to further provide capillary action or wicking properties to direct moisture in the horizontal direction. Further, the barrier layer 308, similar to the barrier layer 208 of FIGS. 2-3, is typically polyethylene (PE) which provides a barrier to prevent moisture penetration to a support surface or frame beneath the incontinence detection pad 200. Like the barrier layer 208, the barrier layer 308 also includes a moisture detection sensor system 112 for detecting moisture presence. As discussed above, the moisture detection sensor system 112 includes a plurality of electrodes 114 and a moisture sensor 116. In the illustrative embodiment, the plurality of electrodes 114 is printed directly onto a top surface of the barrier layer 308 that faces the absorbent layer 306.

The absorbent layer 306, similar to the absorbent layer 206 of FIG. 2, includes an absorbent material arranged within the absorbent layer 206 to form a density gradient to provide capillary action or wicking properties to direct moisture away from the targeted region 312. To do so, in the illustrative embodiment, an increasing density gradient is preferably formed from the targeted region 312 outwardly toward peripheral regions of the incontinence detection pad 300 as shown in FIG. 5. In other words, the absorbent material is more densely packed at the peripheral regions of the absorbent layer 306 compared to the absorbent material at the targeted region 312. Such structural arrangement of the absorbent material allows moisture to be drawn away from the targeted region 312 toward the peripheral regions of the absorbent layer 306. In some embodiments, an increasing density gradient is also formed downwardly from a top surface to a bottom surface of the absorbent layer 306 in the thickness direction. Such structural arrangement of the absorbent material provides capillary action or wicking properties to direct moisture in a vertical direction toward a bottom surface of the absorbent layer 306. As discussed above, the barrier layer 308 includes the moisture detection sensor system 112 facing the absorbent layer 306. As such, the downward density gradient of the absorbent layer 306 is configured to quickly draw the moisture downwardly toward the bottom of the absorbent layer 306 close to the moisture detection sensor system 112 for faster detection than if no density gradient were provided.

As shown in FIG. 5, the illustrative absorbent layer 306 further includes embossed areas 310 that are compressed into a pre-determined shape or pattern. In the illustrative embodiment, the embossed areas 310 form a sinusoidal wave pattern that extends generally horizontally across the absorbent layer 306 perpendicular to the vertical segments 124, 126 of the electrodes 114. It should be appreciated that the pattern of the embossed areas 310 may be any shape or pattern. It should be appreciated, however, the pattern is preferably non-intersecting lines, such as, sinusoidal waves or zig-zag lines, that generally extends horizontally across the absorbent layer 306. Such arrangement is configured to enhance the directional wicking of moisture toward the peripheral regions of the absorbent layer 306 in a direction perpendicular to the vertical segments 124, 126 of the moisture detection sensor system 112. As such, the directional wicking property of the moisture detection pad 300 establishes faster detection by quickly spreading out moisture horizontally between the vertical segments 124, 126 or between any one of the first set of the electrode segments 120, 122, 126 and any one of the second set of electrode segments 118, 124 for faster detection, as discussed in detail above.

Referring now to FIGS. 6 and 7, a portion of the absorbent layer 306 is shown. As shown in FIG. 6, the embossed areas 310 of the absorbent layer 306 are positioned between non-embossed areas 316 of the absorbent layer 306. A cross-section of a portion of the absorbent layer 306 is shown in FIG. 7 to illustrate the embossed areas 310 and the non-embossed areas 316. The embossed areas 310 define one or more grooves 320 between the distribution layer 304 and the absorbent layer 306. Such grooves 320 are formed as a result of compressing the absorbent layer 306 to create the embossed areas 310. In the illustrative embodiment, the grooves 320 are formed substantially horizontally along the absorbent layer 306 toward the peripheral regions of the absorbent layer 306 in a direction perpendicular to the vertical segments 124, 126 of the electrodes 114. The grooves 320 are adapted to provide flowpaths to guide moisture or fluid away from the targeted region 312 toward the peripheral regions along the grooves 320. As such, the grooves 320, in addition to the acquisition and distribution layers 302, 304, are configured to distribute moisture away in a direction perpendicular to the vertical electrode segments 124, 126 of the moisture detection sensor system 112 to achieve faster moisture detection.

In addition, the embossed areas 310 further define one or more capillary pathways extending substantially horizontally along the absorbent layer 306 toward the peripheral regions of the absorbent layer 306 in a direction perpendicular to the vertical electrode segments 124, 126 of the moisture detection sensor system 112. The capillary pathways include the compressed absorbent material of the embossed areas 310. As shown in FIG. 7, the compression of the absorbent material in the embossed areas 310 results in a different density of fibers or material as compared to the non-embossed areas 316. In other words, a density of the absorbent material in the embossed area 310 is higher than a density of the absorbent material in the non-embossed area 316 of the absorbent layer 306. The difference in density of the absorbent material allows the moisture to wick from the non-embossed area 316 (i.e., the low density area) to the embossed area 310 (i.e., the high density areas) as indicated by arrows 318 in FIG. 7. As a result, the moisture is more concentrated along the embossed areas 310 and further travels downward in the embossed areas 310 toward the moisture detection sensor system 112 of the barrier layer 30 for faster moisture detection. It should be appreciated that in some embodiments, the acquisition layer 302, the distribution layer 304, and the absorbent layer 306 of the moisture detection pad 300 may be compressed to form embossed areas.

In addition to the combination of the horizontal orientation of the nonwoven material of the acquisition and distribution layers 302, 304 and the horizontal density gradient of the absorbent material of the absorbent layer 306, the embossed areas 310 further enhance the wicking property of the moisture detection pad and draw moisture in the horizontal direction 314, shown in FIG. 5, from the targeted region 312 faster toward peripheral regions of the absorbent layer 306 in a direction perpendicular to the vertical segments 124, 126 of the electrodes 114. As such, the embossing feature of the moisture detection pad 300 further enhances the directional wicking property of the incontinence detection pad 300 for faster detection and reduction of false positives for incontinence detection caused by perspiration or other undesirable moisture detection.

Figure 8:
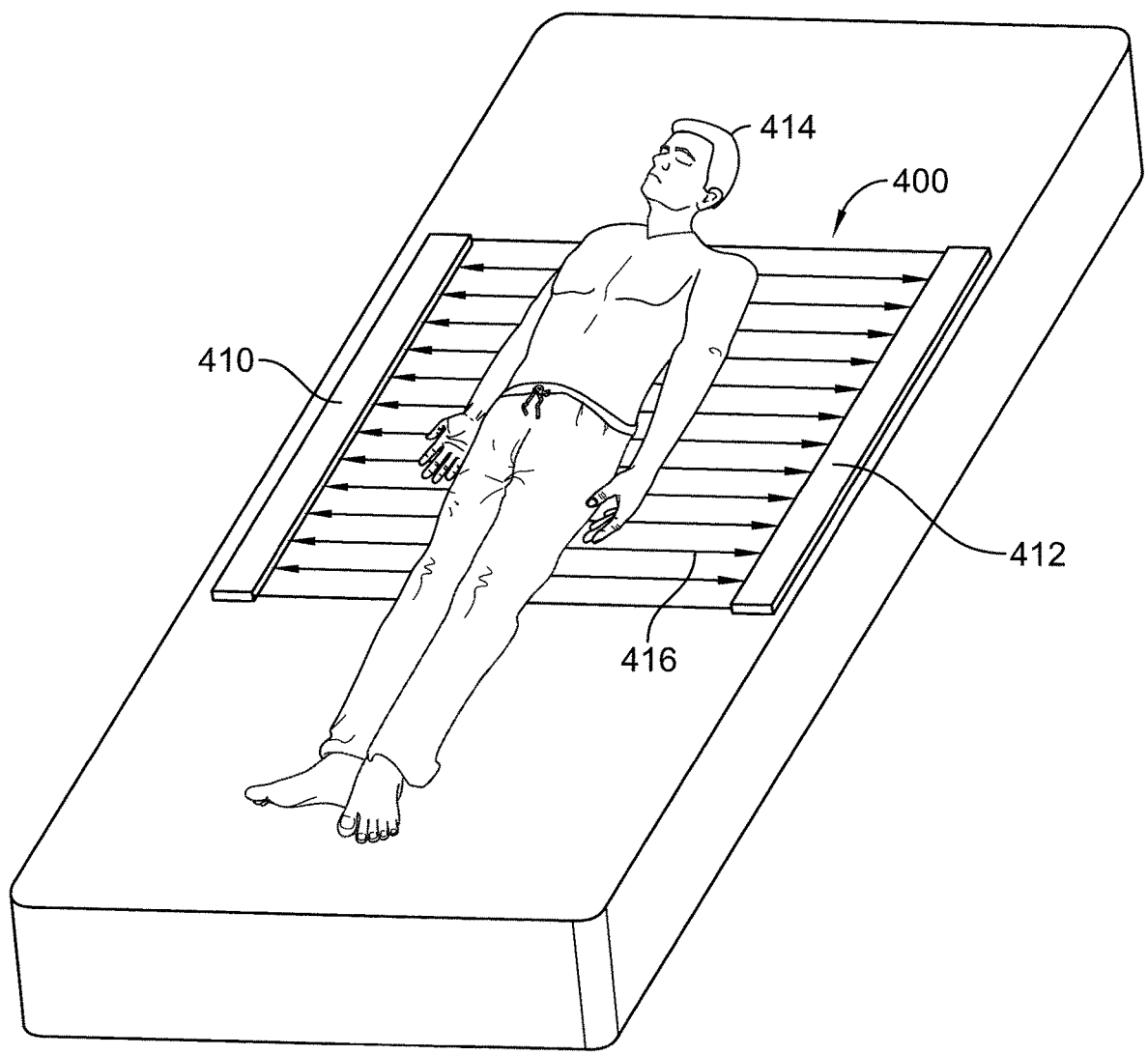
FIG. 8 is a schematic perspective view of a third embodiment of an incontinence detection pad with absorbent blocks positioned on each side of the incontinence detection pad.

Referring now to FIG. 8, an illustrative incontinence detection pad 400 is shown. The incontinence detection pad 400 includes two absorbent blocks 410, 412 and one of the moisture detection pads 100, 200, 300. In the illustrative embodiment, each absorbent block 410, 412 is coupled to the incontinence detection pad 100, 200, 300 on a respective side, such that the nonwoven moisture-wicking material of acquisition and distribution layers of the moisture detection pad 100, 200, 300 extend from the first absorbent block 410 on a first side of the incontinence detection pad 400 (i.e., the patient's right side when a patient 414 is lying supine on the continence detection pad 400) to the second absorbent block 412 on a second side of the incontinence detection pad 400 (i.e., the patient's left side when the patient 414 is lying supine on the continence detection pad 400). The absorbent blocks 410, 412 are adapted to absorb the moisture that has been wicked toward the first and second sides of the incontinence detection pad 400 in the horizontal direction in order to provide a greater moisture storage. It should be appreciated that in some embodiments, the moisture detection pad 100, 200, 300 may be surrounded by absorbent blocks similar to the blocks 410, 412.

Figure 9:
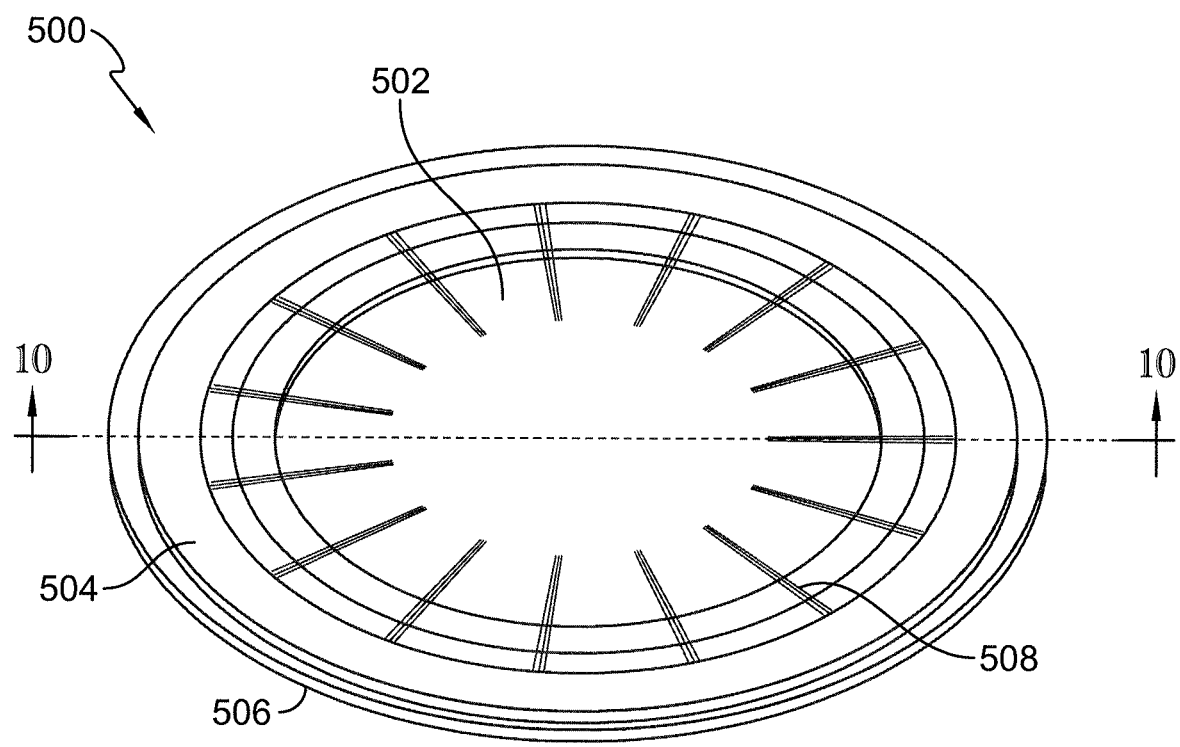
FIG. 9 is a plan view of a moisture-wicking dressing.
Figure 10:
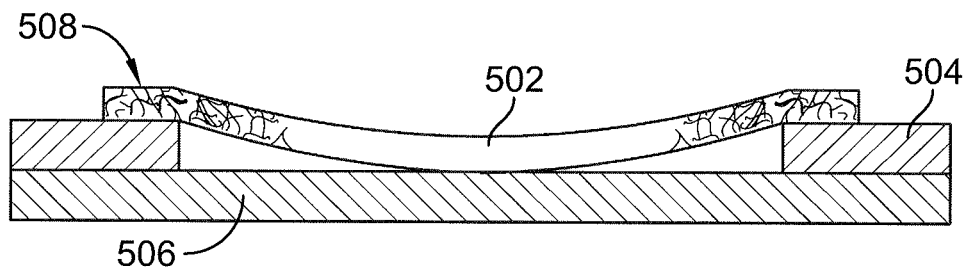
FIG. 10 is a cross-sectional view of the moisture-wicking dressing of FIG. 9 taken along line 10-10 of FIG. 9.

Referring now to FIGS. 9 and 10, a moisture-wicking dressing 500 is shown. The moisture-wicking dressing 500 is constructed of soft, compliant material with layers that slide readily over one another so that the moisture-wicking dressing 500 imposes limited pressure and shear to the vulnerable site. In the illustrative embodiment, the moisture-wicking dressing 500 comprises an upper layer 502, an absorbent layer 504 positioned at a perimeter of the moisture-wicking dressing 500, and a lower layer 506. The upper layer 502 includes a moisture-wicking material that forms a plurality of capillary pathways 508 extending from a center of the moisture-wicking dressing 500 toward the absorbent material 504 at the perimeter of the moisture-wicking dressing 500. The capillary pathway 508 is made of a high density of the moisture-wicking material configured to draw moisture away from the center of the moisture-wicking dressing 500. For example, in the illustrative embodiment, the moisture-wicking material is nonwoven and non-linear polymeric or pulp fibers that are horizontally oriented into a nonwoven web structure. In some embodiments, the moisture-wicking material may be a three-dimensional fibrous or woven material. The orientation of the capillary pathways 508 is adapted to provide capillary action or wicking properties to direct moisture in a horizontal direction to draw the moisture toward peripheral regions of the upper layer 502.

As discussed above and shown in FIG. 10, the absorbent layer 504 is positioned at an outer perimeter of the upper layer 502. In some embodiments, the absorbent layer 504 may be positioned between the upper layer 502 and the lower layer 506. In such embodiment, the absorbent layer 504 may be adapted to be in contact with the skin at an anatomic site and with the upper layer 502. Lastly, the lower layer 506 has an adhesive lower surface capable of adhering to a person's skin surrounding an anatomic site. The adhesive is provided only in the peripheral area of lower layer 506 in some embodiments.

Figure 11:
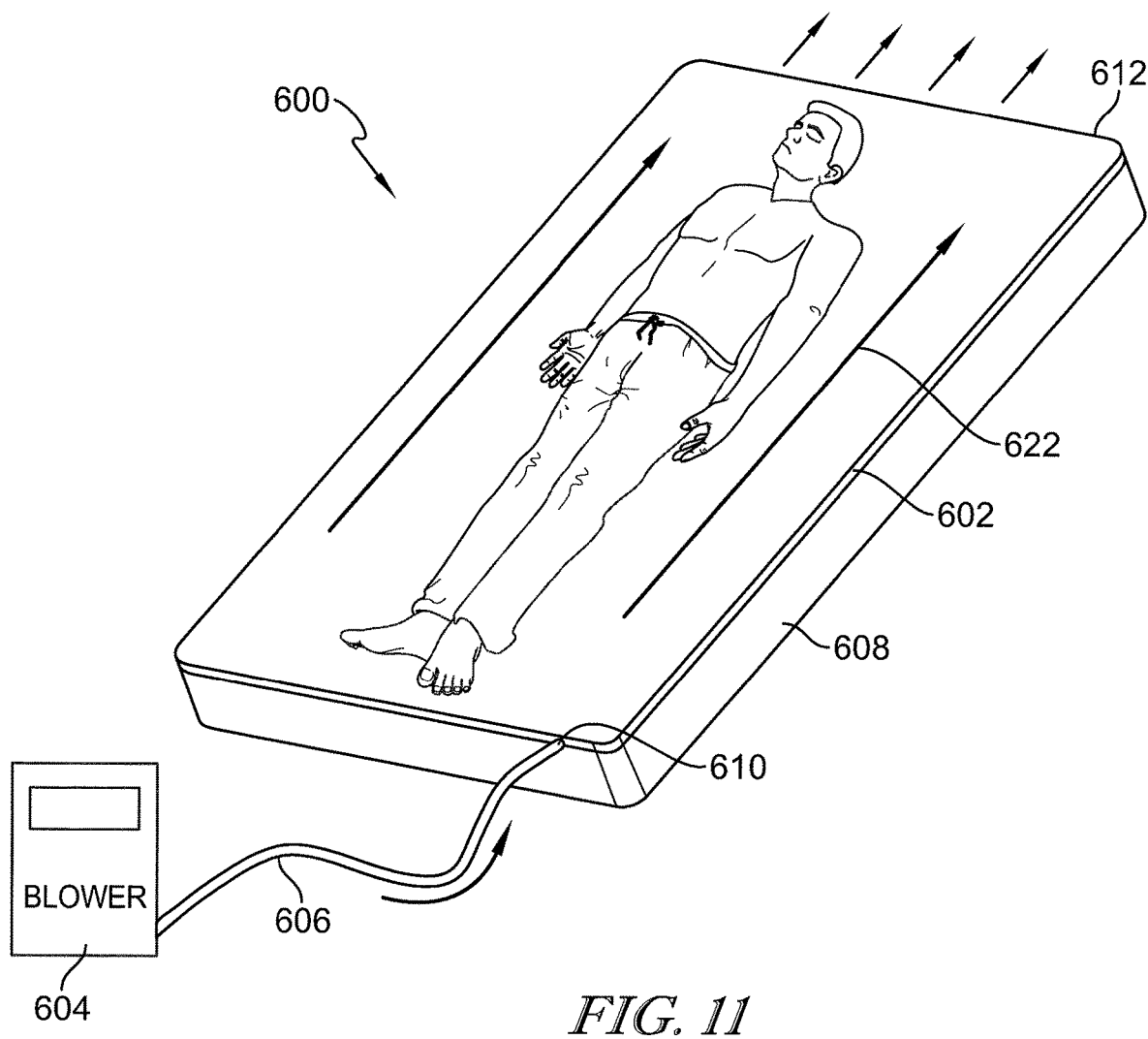
FIG. 11 is a schematic perspective view of a microclimate management topper system.
Figure 12:
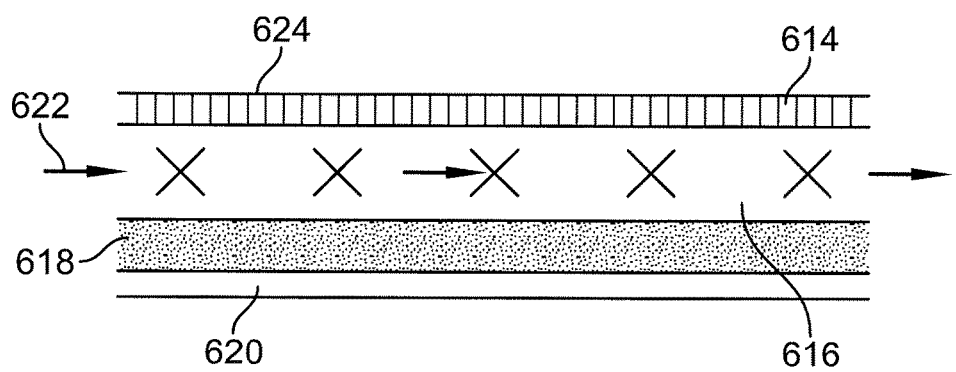
FIG. 12 is a cross-sectional view of a microclimate management topper of the microclimate management topper system of FIG. 10.

Referring now to FIGS. 11 and 12, an illustrative microclimate management topper system 600 is shown. The microclimate management topper system 600 includes a microclimate management topper 602 and a blower 704 removably coupled to the microclimate management topper 602 via a conduit 606. In the illustrative embodiment, the fluid supply 604 is an air blower 604 that can supply pressurized air into the microclimate management topper 602. It should be appreciated that the blower 604 can supply a various other gasses and/or liquids. In some embodiments, the blower 604 may be directly connected to the microclimate management topper 602. In other embodiments, the blower 604 may be integrated or partially integrated within a patient support apparatus 608, such as a mattress. It should be appreciated that, in some embodiments, the blower 604 may further include a heating element (not shown) and/or cooling element (not shown) that can heat and/or cool the fluid being supplied.

The microclimate management topper 602 is configured to be positioned atop the patient support apparatus 608. The microclimate management topper 602 further includes a fluid inlet 610 and a fluid outlet 612. In the illustrative embodiment, the fluid inlet 610 is positioned at a foot end of the patient lying supine on the microclimate management topper 602, and the fluid outlet 612 is positioned along a side of the microclimate management topper 602 at a head end of the patient lying supine on the microclimate management topper 602 opposite the fluid inlet 610. It should be appreciated that in some embodiments, the fluid inlet and the fluid outlet may be positioned on each side of the patient lying supine on the microclimate management topper 602.

As shown in FIG. 12, the microclimate management topper 602 includes an upper layer 614, a spacer layer 616, an absorbent layer 618, and a barrier layer 620. In the illustrative embodiment, the upper layer 614 is liquid permeable, the absorbent layer 618 is air permeable, and the barrier layer 620 is liquid impermeable to prevent any moisture from leak into the patient support apparatus 608. The upper layer 614 includes a moisture-wicking material. In the illustrative embodiment, the moisture-wicking material is nonwoven and non-linear polymeric or pulp fibers that are generally oriented vertically from an upper surface 624 of microclimate management topper 602 downwardly toward the spacer layer 616. Such orientation of the moisture-wicking material of the upper layer 614 is adapted to provide capillary action or wicking properties to direct moisture in downward direction to draw the moisture away from the upper surface 624 positioned against the patient's skin. In some embodiments, the moisture-wicking material may be interwoven polymeric or pulp fibers that are generally oriented vertically from an upper surface 624 of the microclimate management topper 602 downwardly toward the spacer layer 616.

The spacer layer 616 includes the fluid inlet 610 on a patient's foot end of the microclimate management topper 602 and the fluid outlet 612 a patient's head end of the microclimate management topper 602. The spacer layer 616 also includes a three-dimensional material between the fluid inlet 610 and the fluid outlet 612. The spacer layer 616 further includes a moisture-wicking material. In the illustrative embodiment, the moisture-wicking material is interwoven polymeric or pulp fibers. The three-dimensional material and moisture-wicking material of the spacer layer 616 are air permeable and allows air from the blower 604 to flow along the spacer layer 616 from the fluid inlet 610 to the fluid outlet 612, as indicated by arrows 622 in FIGS. 11 and 12. The spacer layer 616 is configured to conduct air between the upper layer 614 and the absorbent layer 616 of the microclimate management topper 602, and draw the moisture away from the patient toward the fluid outlet 612. The fluid outlet 612 is defined by the three-dimensional material exposed on the patient's head end of the moisture wicking layer 616 of the microclimate management topper 602. This allows air and moisture to exit the microclimate management topper 602.

Once the moisture reaches the spacer layer 616, the moisture is carried away from evaporation by air flowing through the spacer layer 616 of the microclimate management topper 602. Additionally, the remaining moisture may be absorbed into the absorbent layer 618, which may then be evaporated by the air flowing through the spacer layer 616. As described above, the air from the blower 604 flows across the spacer layer 616 from the fluid inlet 610 to the fluid outlet 612. Accordingly, the cooled-vapor from evaporation is directed toward the fluid outlet 612 to exit the microclimate management topper 602. In addition, because the blower 604 provides pressurized air, the cooled-vapor from evaporation may be pushed upwardly toward the upper layer 614 of the microclimate management topper 602. This not only removes the moisture at the upper surface 624 of the microclimate management topper 602, but also facilitates to cool and dry the patient's skin around the interface of the patient's skin with the upper surface 624 of the microclimate management topper 602. Further, the pressure from the blower 604 allows the air to maintain its flowpath 622, thus preventing the moisture from reverse flow into the blower 604. In some embodiments, the microclimate management topper 602 may further include a check valve (not shown) near the fluid inlet 610, which automatically prevents liquid from overflowing into the blower 604 while providing the air through the fluid inlet 610. In other embodiments, other types of check valve may be used.

In some embodiments, the microclimate management topper system 600 may include a moisture detection sensor system 112 for detecting the presence of moisture. The moisture detection sensor system 112 may be embedded in the barrier layer 620 of microclimate management topper 602 and is similar to the moisture detection sensor system 112 described above in the embodiments of FIGS. 1-8.

Referring now to FIGS. 13-16, exemplary schematics of embodiments of a moisture detection system 812, 912, 1012, 1112 are shown. It should be appreciated that any one of the moisture detection systems 812, 912, 1012, 1112 may be used with any one of the incontinence detection pads 100, 200, 300, 400 shown in FIGS. 1-8. The moisture detection system 812, 912, 1012, 1112 are configured to prevent false positive detections of incontinence events caused by erratic operation of the moisture detection system. Similar to the moisture detection sensor system 112 discussed above, the moisture detection systems 812, 912, 1012, 1112 include a plurality of electrodes 814, 914, 1014, 1114, respectively, and a moisture detection sensor 816, 916, 1016, 1116, respectively. The moisture detection sensor 816, 916, 1016, 1116 may be embodied as an RFID tag, for example.

The RFID tag 816, 916, 1016, 1116 is a passive tag or chip that communicates with an associated reader by using the electromagnetic field generated by an associated RFID reader to power the RFID tag 816, 916, 1016, 1116. In some embodiments, semi-passive or active RFID tags are used. Additionally, the RFID tag 816, 916, 1016, 1116 is configured to communicate with the RFID reader to send stored data, and the RFID reader or other processing circuitry determines whether the incontinence pad is wet or dry by evaluating the data transmitted from the RFID tag 816, 916, 1016, 1116. In the illustrative embodiments shown in FIGS. 13-16, the RFID tags 816, 916, 1016, 1116 include a tamper input, which is configured to activate an alert signal when the moisture detection system 812, 912, 1012, 1112 is completed (e.g., a closed circuit) by moisture connecting the electrodes 814, 914, 1014, 1114. It should be noted that during the transfer of electromotive forces (EMF) from RFID reader to power the RFID tag 816, 916, 1016, 1116, the EMF may enter the tamper input of the RFID tag 816, 916, 1016, 1116, which may cause erratic operation of the moisture detection systems 812, 912, 1012, 1112. To prevent false positives caused by such erratic operation of the moisture detection systems 812, 912, 1012, 1112, a different mechanism may be implemented in the moisture detection system 812, 912, 1012, 1112.

In the illustrative embodiments, the moisture detection systems 812, 912, 1012, 1112 operate at about 915 MHz. It should be appreciated that in some embodiments, other frequencies may be used. An incontinence pad typically requires the plurality of electrodes 814, 914, 1014, 1114 to extend about 32 long from the RFID tag 816, 916, 1016, 1116 to cover the length of the incontinence pad for efficient detection. Additionally, this makes it efficient at coupling in the 915 MHz energy used to power the RFID tag 816, 916, 1016, 1116 as well as communicate with the RFID reader.

Figure 13:
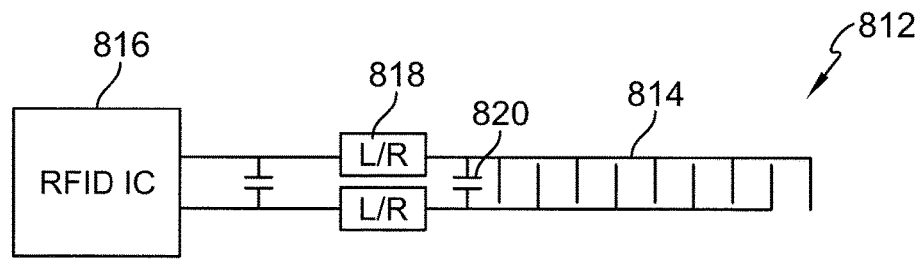
FIGS. 13-16 are diagrams of moisture detection systems configured to prevent false positive detections of incontinence events caused by erratic operation of the moisture detection system.
Figure 14:
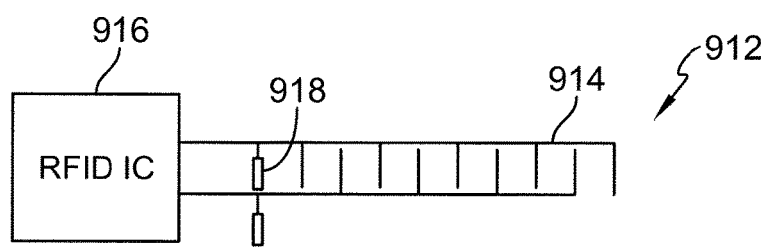

The moisture detection system 812 shown in FIG. 13 further includes resistor inductor units (L/R) 818 and capacitors 820 that are configured to suppress noise of the RFID tag 816. Whereas, the moisture detection system 912 shown in FIG. 14 further includes a plurality of quarter wave resonant stubs 918 positioned close to the RFID tag. In the illustrative embodiment, the quarter wave resonant stubs 918 are positioned between the RFID tag and any vertical segments of the electrodes 914. The quarter wave resonant stubs 918 are configured to produce a resonant frequency at the center of the RFID band, for example, US RFID band from 900-928 MHz. At 915 MHz, ¼λ works out to be approximately 3 inches long. Of course, it should be appreciated that in some embodiments, other frequency band range may be used. The stubs are configured to eliminate the 915 MHz energy from the input in the following way: the stubs are ¼λ long and unterminated. A wave traveling down the transmission line will be reflected from the unterminated end of the transmission line and travel back toward the opposite end of the stub. When the reflected wave arrives back at the end it entered, it will be exactly 180 degrees out of phase with the energy incident from the detection grid, thereby cancelling the 915 MHz field out at the tamper input.

Figure 15:
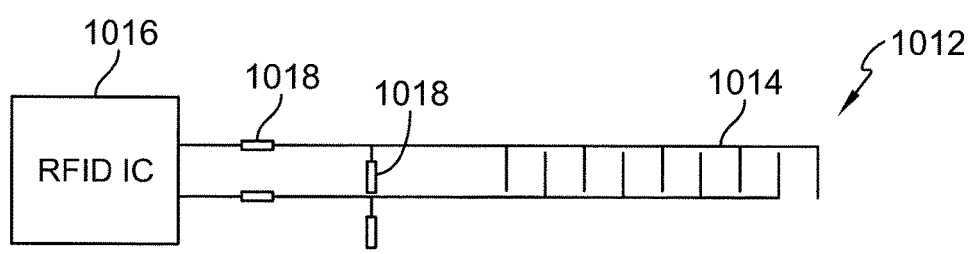

Referring now to FIG. 15, the moisture detection system 1012 includes a plurality of radial stubs 1018. The radial stub 918 is a more broadband ¼λ, stub. In the illustrative embodiments, the moisture detection system 1012 includes four radial stubs 918: two of 60° included angle stubs and two of 90° included angle stubs. Such combination of stubs may allow a universal suppression network that can operate in both the European 860 MHz band as well as the US 915 MHz band without change. Additionally, in some embodiments, a phasing and matching network 1020 may be added to the moisture detection system 1012, as shown in FIG. 16.

Figure 16:
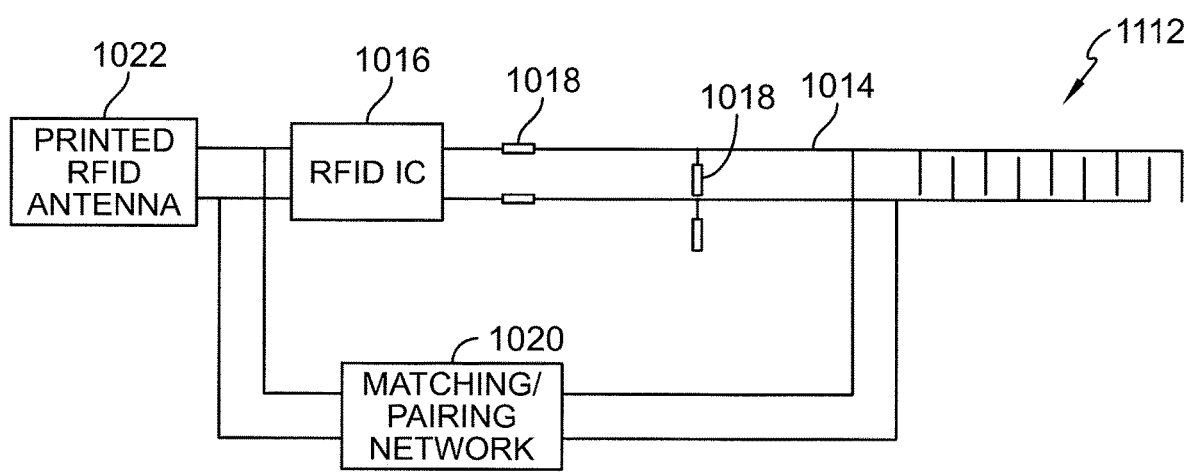

Referring to FIG. 16, the moisture detection system 1112 includes a phasing and matching network 1020 and printed RFID antenna 1022 added to the moisture detection system 1012. In other words, the phasing and matching network 1020 is configured to couple the moisture detection system 1012 to the RFID transmit/receive antenna 1022 and match the complex impedance of the moisture detection system 1112 to the input impedance of the RFID chip/antenna, which is generally (24-j222Ω), assuming the antenna presents the characteristic impedance of the input. Such construction creates constructive interference as opposed to destructive interference at the tamper input pins.

Figure 17A:
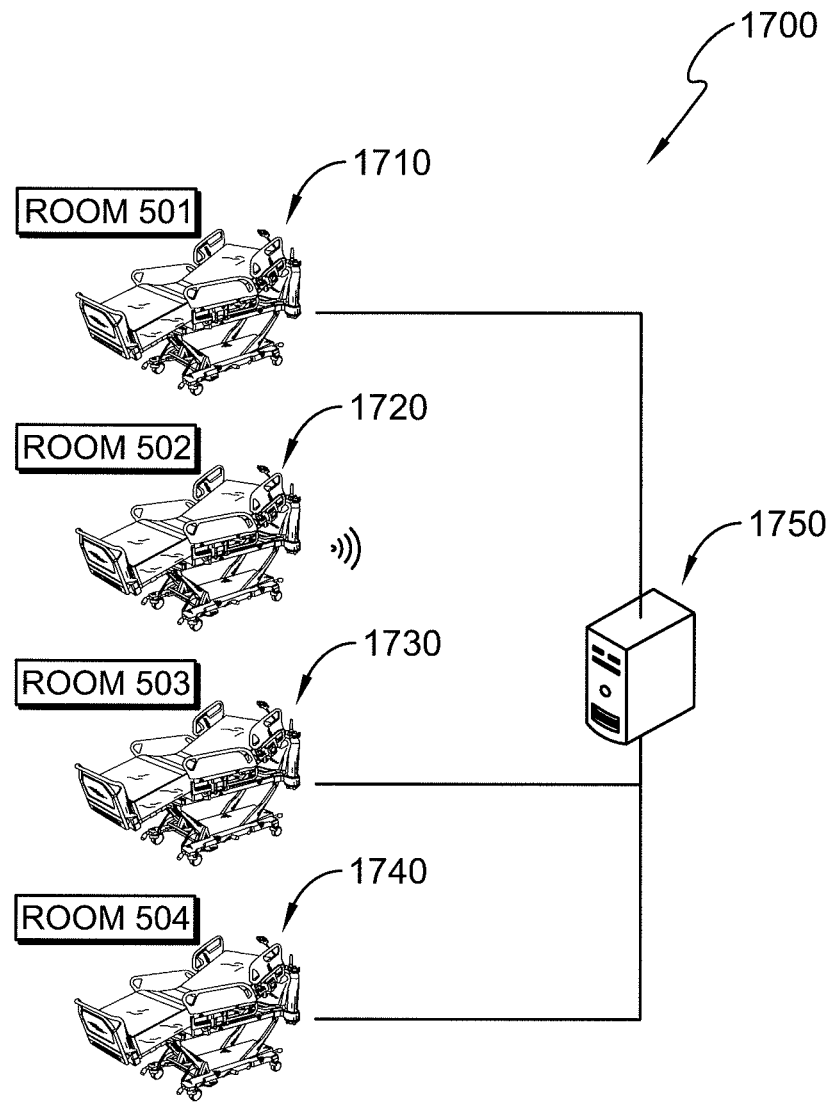
FIG. 17A-D is a pairing process between a primary device and a secondary device such that the secondary device is associated with a location of the primary device.

Now referring to FIGS. 17A-D, a pairing process between a primary device and a secondary device such that the secondary device is associated with a location of the primary device is shown. For example, in the illustrative embodiment, the primary device is embodied as a patient support apparatus (e.g., a bed). The location of the bed is determined using either a wired connection to a communication unit on a room or a wireless connection to a Real Time Locating System (RTLS). For example, as shown in FIG. 17A, the beds 1710, 1730, 1740 are connected to the server 1750 using the wired connection, whereas, the bed 1720 is connected to the server 1750 using the wireless RTLS. As shown in the table of FIG. 17A, each bed has a unique identification number ("BED ID"). The server 1750 determines the bed 1710 is located in Room 501, the bed 1720 is located in Room 502, the bed 1730 is located in Room 503, and the bed 1740 is located in Room 504. The server 1750 is configured to associate the location of the bed with the corresponding BED ID, such that when the bed sends data to the server 1750, the data is associated with the location of the bed.

Figure 17B:
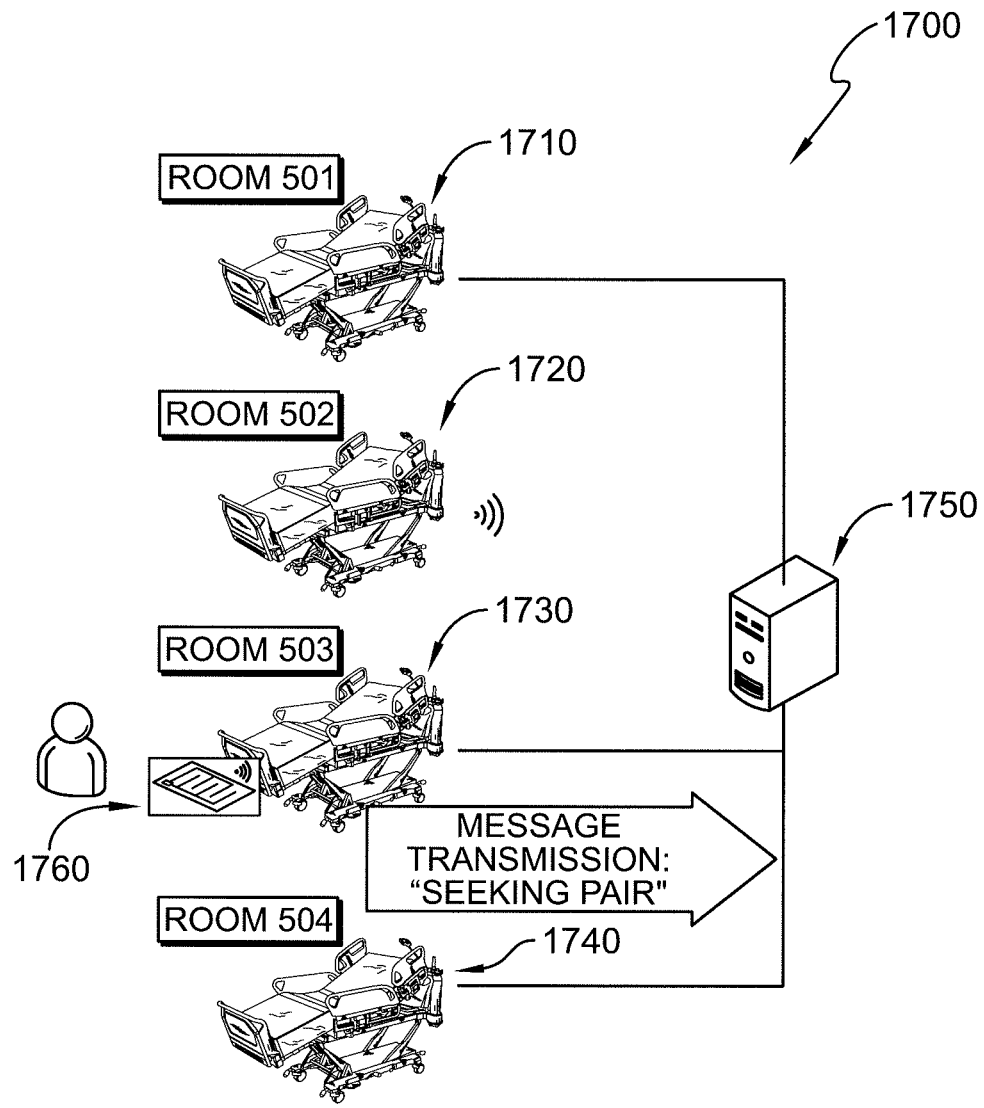
Figure 17C:
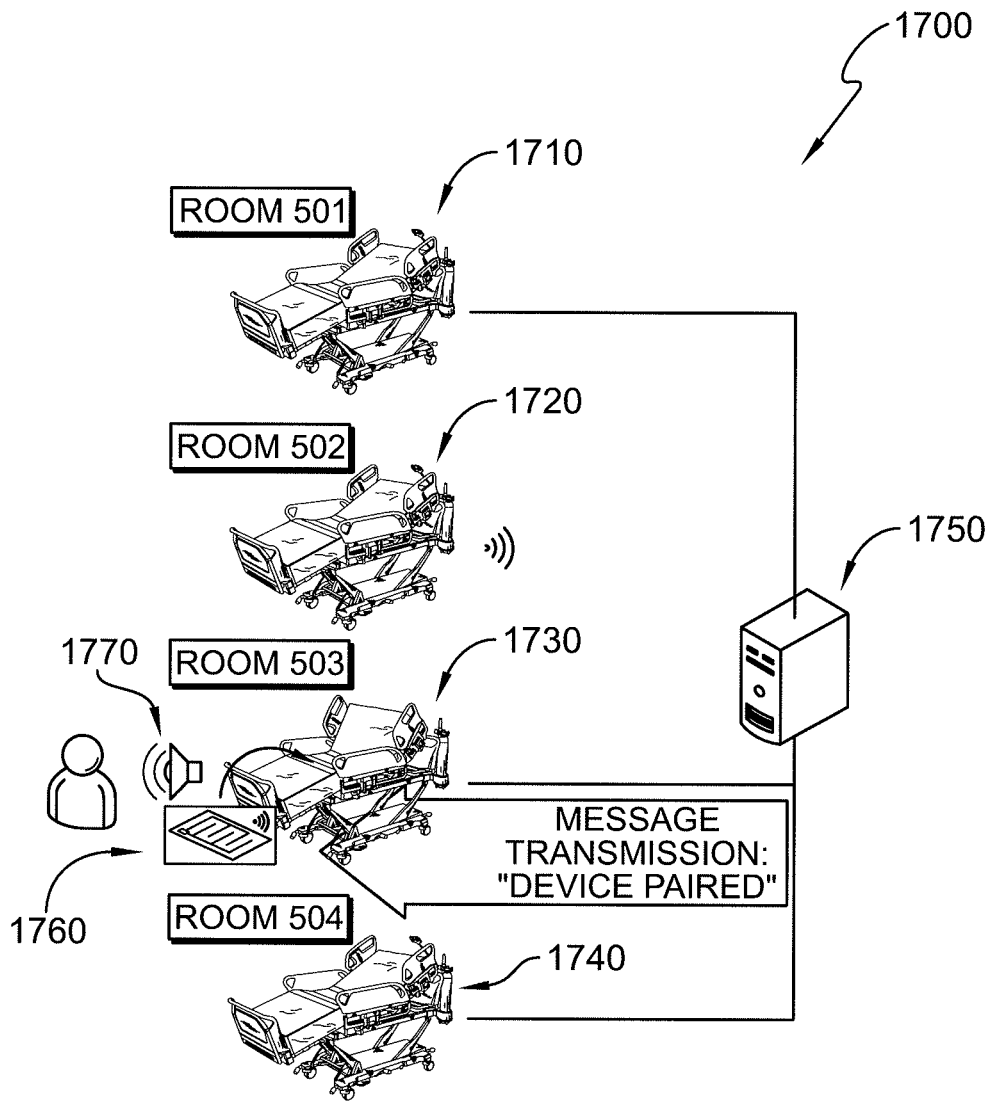
Figure 17D:
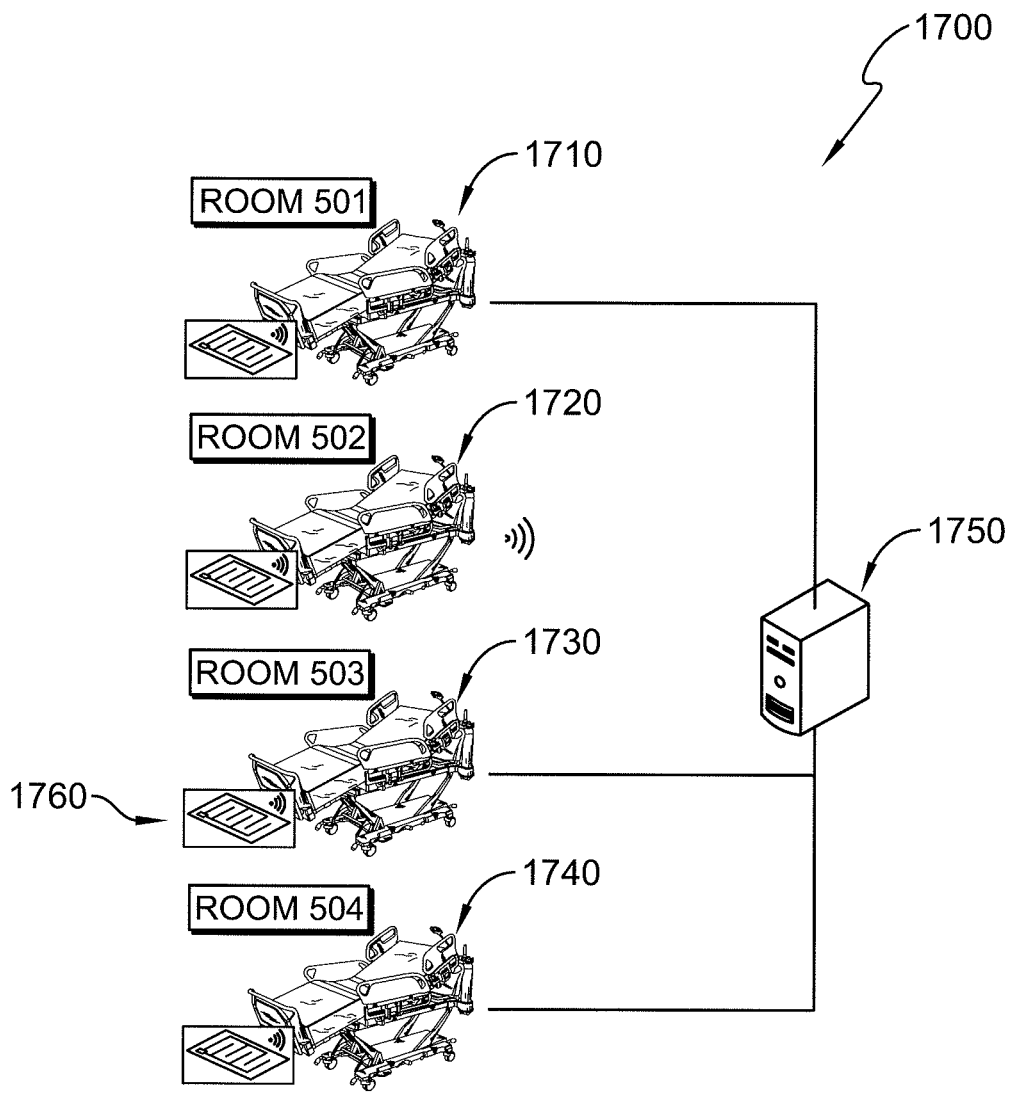

As shown in FIG. 17B, a secondary device 1760, such as an incontinence detection pad, may be mounted, attached, or placed on a bed. In the illustrative embodiment, the secondary device 1760 is embodied as an incontinence detection pad 1760 and is placed on the bed 1730. When the incontinence detection pad 1760 is initially placed on the bed 1730, a corresponding reader that communicates with the incontinence detection pad 1760 is configured to communicate with the server 1750. It should be appreciated that some secondary devices may communicate directly with the server 1750 using a wireless connection. In case of the incontinence detection pad 1760, the incontinence detection pad 1760 is configured to communicate with a corresponding reader, which in turns communicates with the server 1750. When the incontinence detection pad 1760 is in a "pairing mode," the corresponding reader sends a message to the server 1750 to inform that the incontinence detection pad 1760 is seeking a corresponding primary device (e.g., the corresponding bed 1730 in the illustrative embodiment). The server 1750 then commences monitoring the primary devices connected for a distinct key. It should be appreciated that the distinct key may be defined by a manufacturer, a provider, or a user. The distinct key may be a sequence of events to transmit existing data points from the bed that are unlikely to occur on any other bed. For example, the bed could be placed in a position with the head angle greater than 60 degrees with all side rails down, or a single side rail could be raised and lowered five times within 10 seconds. Once the server 1750 detects the distinct key, the server 1750 associates the secondary device 1760 with that bed, and informs the secondary device 1760 that it is now paired as shown in FIG. 17C. In some embodiments, the secondary device 1760 may confirm the pairing with a brief visual or audible indication. It should be appreciated that each secondary device may be associated with the location of the primary device 1710, 1720, 1730, 1740 as shown in the table in FIG. 17D.

It should also be appreciated that the pairing process 1700 enables a secondary device to be paired to the bed with no changes to the bed architecture, so that the server is able to associate that secondary device to the beds location. Identifying a location is desirable if these secondary devices are to send any type of data. For example, when an incontinence detection pad transmits incontinence event data, information about the location of the incontinence event is needed to make the data meaningful. It should be appreciated that in some embodiments, the primary and secondary devices may be paired using Bluetooth technology.

Although certain illustrative embodiments and graphical illustrations have been described in detail above, variations and modifications exist within the scope and spirit of this disclosure as described and as defined in the following claims.

The invention claimed is:

1. An incontinence detection pad comprising:
    a moisture absorbent layer having (i) non-embossed areas with a first density of fibers of the moisture absorbent layer and (ii) embossed areas with a second density of fibers of the moisture absorbent layer, the second density being greater than the first density, wherein the embossed areas comprise grooves that are provided in a top surface and a bottom surface of the moisture absorbent layer with respective pairs of the grooves in the top and bottom surfaces being aligned with each other,
    a plurality of electrodes positioned beneath the moisture absorbent layer, wherein the plurality electrodes are arranged in an interdigitated pattern,
    a transmitter connected to the plurality of electrodes and configured to transmit a signal indicative of a status of the moisture absorbent layer, wherein the transmitter includes a radio frequency identification (RFID) tag and antenna, and
    a pair of quarter wave resonant stubs each being spaced from the antenna and coupled to a respective one of the electrodes of the plurality of electrodes.

2. The incontinence detection pad of claim 1, wherein the embossed areas are configured to draw moisture toward a peripheral region of the incontinence detection pad.

3. The incontinence detection pad of claim 1, further including a top layer positioned atop the moisture absorbent layer, wherein the top layer includes a nonwoven moisture-wicking material that is oriented horizontally along the top layer.

4. The incontinence detection pad of claim 1, wherein the plurality of electrodes is printed on a barrier layer positioned underneath the moisture absorbent layer.

5. The incontinence detection pad of claim 1, wherein the moisture absorbent layer includes a moisture absorbent material forming an increasing density gradient and wherein the increasing density gradient is formed from a top surface to a bottom surface of the moisture absorbent layer.

6. The incontinence detection pad of claim 1, wherein the RFID tag comprises a passive RFID tag.

7. The incontinence detection pad of claim 1, wherein the transmitter is configured to communicate with a reader that evaluates the transmitted signal to determine the status of the moisture absorbent layer.

8. The incontinence detection pad of claim 7, wherein the reader is an RFID reader.

9. The incontinence detection pad of claim 7, wherein the reader is further configured to wirelessly communicate with a server to alert a caregiver of the status of the moisture absorbent layer.

10. The incontinence detection pad of claim 9, wherein the server is included in a nurse call system or in an electronic medical record (EMR) system.

11. The incontinence detection pad of claim 7, wherein the reader is further configured to communicate with a server to alert a caregiver of the status of the moisture absorbent layer via a wired connection.

12. The incontinence detection pad of claim 11, wherein the wired connection comprises a nurse call cable.

13. The incontinence detection pad of claim 7, wherein the reader is further configured to communicate with a notification system to alert a caregiver of the status of the moisture absorbent layer.

14. The incontinence detection pad of claim 1, wherein the embossed areas are compressed into a pre-determined pattern.

15. The incontinence detection pad of claim 1, wherein the embossed areas form a sinusoidal wave pattern.

16. The incontinence detection pad of claim 1, wherein the embossed areas form a zig-zag pattern.

17. The incontinence detection pad of claim 1, wherein the embossed areas form a pattern having non-intersecting lines.

18. The incontinence detection pad of claim 1, wherein the embossed areas form a pattern having non-intersecting lines that horizontally extend along the moisture absorbent layer.

19. The incontinence detection pad of claim 1, wherein each quarter wave resonant stub is interposed between the RFID tag and each respective electrode of the plurality of electrodes.

20. The incontinence detection pad of claim 1, further comprising a phasing and matching network coupled to the plurality of electrodes.

* * * * *